United States Patent [19]

Richardson et al.

[11] Patent Number: 4,529,799
[45] Date of Patent: Jul. 16, 1985

[54] BIS-PYRIDYL CONTAINING TRIAZOLES

[75] Inventors: Kenneth Richardson; Peter J. Whittle, both of Canterbury, England

[73] Assignee: Pfizer Inc., New York, N.Y.

[21] Appl. No.: 519,656

[22] Filed: Aug. 2, 1983

[30] Foreign Application Priority Data

Aug. 7, 1982 [GB] United Kingdom ................ 8222849

[51] Int. Cl.³ .......................................... C07D 401/14
[52] U.S. Cl. .................................... 546/256; 546/276;
[58] Field of Search ................ 546/256, 276; 424/263

[56] References Cited

FOREIGN PATENT DOCUMENTS 0052424 5/1982 European Pat. Off. ............ 546/276
0046337 2/1983 European Pat. Off. .

Primary Examiner—Jane T. Fan
Attorney, Agent, or Firm—Charles J. Knuth; Albert E. Frost; James M. McManus

[57] ABSTRACT

Compounds of the formula

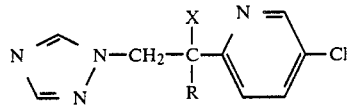

wherein X is halo and R is an aryl group and their pharmaceutically acceptable salts are useful antifungal agents in animals, including man.

3 Claims, No Drawings

BIS-PYRIDYL CONTAINING TRIAZOLES

BACKGROUND OF THE INVENTION

This invention relates to novel 1-aryl-1-(5-chloropyrid-2-yl)-2-(1H-1,2,4-triazol-1-yl)ethyl halide derivatives which are useful in treating fungal infections in animals, including man.

European patent application No. 0046337 discloses a series of substituted 2-(1H-1,2,4-triazol-1-yl)-ethanols as antifungal agents.

Belgian Patent No. 890,741 discloses as antimycotic agents a group of N-(2-chloro-2,3-disubstituted-propyl)imidazoles.

Derivatives of triazole and imidazole are claimed in European patent application No. 0052424 as plant fungicides.

SUMMARY OF THE INVENTION

The compounds of the present invention are of the formula

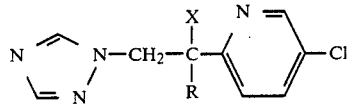

(I)

and the pharmaceutically acceptable acid addition salts thereof, where X is chloro or bromo and R is chloropyridyl or dichlorophenyl.

A preferred group of compounds are those wherein R is chloropyridyl; especially preferred is 1,1-bis(5-chloropyrid-2-yl)-2-(1H-1,2,4-triazol-1-yl)ethyl chloride and 1,1-bis(5-chloropyrid-2-yl)-2-(1H-1,2,4-triazol-1-yl)ethyl bromide.

A second preferred group of compounds are those wherein R is dichlorophenyl; especially preferred is 1-(5-chloropyrid-2-yl)-1-(2,4-dichlorophenyl)-2-(1H-1,2,4,-triazol-1-yl)ethyl chloride and 1-(5-chloropyrid-2-yl)-1-(2,4-dichlorophenyl)-2-(1H-1,2,4-triazol-1-yl)ethyl bromide.

The invention also includes a pharmaceutical composition comprising the aforementioned compounds of the present invention together with a pharmaceutically acceptable diluent or carrier.

Also included as part of the present invention is a method for treating fungal infections in a human being, which comprises administering to said human being an antifungal amount of an aforementioned compound of the present invention or a pharmaceutically acceptable salt thereof.

DETAILED DESCRIPTION OF THE INVENTION

The compounds of the formula (I) can be prepared by the halogenation of the corresponding hydroxy compounds of the formula

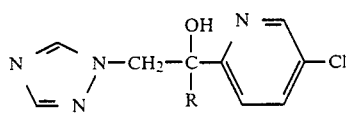

(II)

where R is as defined above, using, as appropriate, thionyl chloride or thionyl bromide.

In a typical procedure using thionyl chloride or bromide, the compound (II) in a suitable solvent, e.g., acetonitrile, is reacted at room temperature with thionyl chloride or bromide, optionally in the presence of a base, preferably imidazole. In some cases heating at up to reflux temperature may be necessary to accelerate the reaction. The product is typically recovered by evaporation of the solvent, followed by the addition of dilute sodium bicarbonate solution to the residue and extraction with ethyl acetate. The organic extracts are dried, evaporated and the residue can then be chromatographed on silica, eluting with e.g., ethyl acetate:-petrol (60°-80°) 1:1. This chromatographic procedure separates the desired product from by-products of the formula

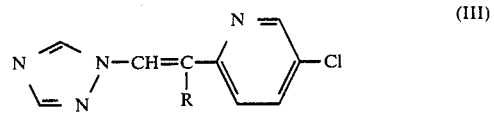

(III)

The starting materials of the formula (II), which are also active as antifungal agents, are obtainable conventionally, see e.g., European patent application No. 0046337, published Feb. 24, 1982. The compounds of the formula (II) in which R is an aromatic heterocyclic group are described in co-pending U.K. patent application No. 8217521 which describes their preparation as follows:

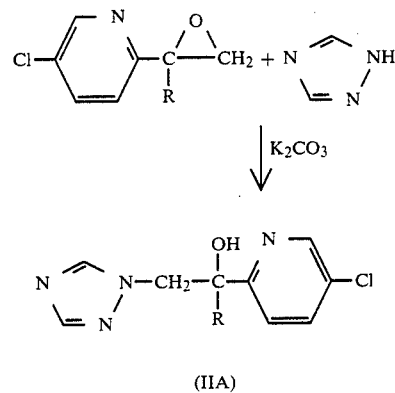

(IIA)

wherein R is said aromatic heterocyclic group. This application also describes the preparation of the oxirane starting materials (VII), e.g., by reacting a halo-substituted derivative (IV) of the desired heterocyclic compound with butyllithium to generate the anion, which is then reacted with the amide (V) prepared from 2-bromo-5-chloropyridine and dimethyl carbamoyl chloride, and the ketone (VI) is converted to the oxirane (VII). This route, where R is again said aromatic heterocyclic group, is shown in the following reaction scheme wherein X is bromo or iodo. In some cases X can be chloro.

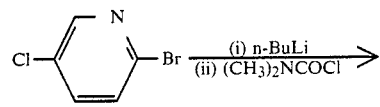

-continued

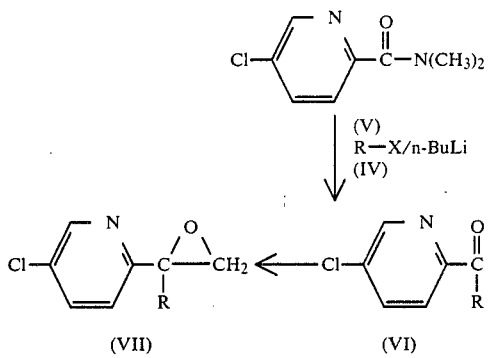

The halo-substituted heterocyclic compounds (IV), preferably the bromo derivatives, are generally known compounds which are either commercially available or they are prepared by conventional methods in accordance with literature precedents.

The amide (V) is simply prepared from 2-bromo-5-chloro-pyridine by reaction first with n-butyllithium to generate the anion, followed by reaction with dimethylcarbamoyl chloride. The reaction is typically achieved in diethyl ether at $-70°$ C.

The ketones (VI) are then prepared by reacting the amide (V) with the anion derived from the appropriate halo-substituted heterocyclic derivative (IV).

In the case of the compound wherein R is 5-chloro-2-pyridyl clearly these two steps can be combined, and the ketone (VI) wherein R is 5-chloro-2-pyridyl can be isolated directed.

The oxiranes (VII) can be obtained from the ketones (VI) by reaction with dimethyloxosulphonium methylide prepared from trimethylsulphoxonium iodide and either sodium hydride in dimethylsulphoxide, or using cetrimide and sodium hydroxide in a mixture of water and toluene or water and trichloroethane.

The reaction using sodium hydride is typically achieved by adding dimethylsulphoxide to a mixture of sodium hydride in dry powdered trimethylsulphoxonium iodide. After stirring for about 30 minutes at room temperature, the ketone (VI) is added in an approximately equimolar amount in dimethylsulphoxide. The reaction mixture may be warmed to accelerate the reaction and after several hours at 50°–80° C., the product can be isolated by conventional procedures.

The reaction utilizing cetrimide is typically achieved by stirring the ketone (VI), trimethylsulphoxonium iodide and cetrimide vigorously together in a mixture of toluene or trichloroethane and sodium hydroxide solution for about an hour at up to about 100° C. The oxirane product can then be isolated by conventional procedures.

It is not generally necessary to isolate the oxirane (VII) and it can be reacted directly with triazole as previously described to give the compound of formula (IIA).

Pharmaceutically acceptable acid addition salts of the compounds of the formula (I) include those formed from strong acids which form non-toxic acid addition salts, such as hydrochloric, hydrobromic, sulphuric, nitric, oxalic and methane sulphonic acids.

The salts may be obtained by conventional procedures, e.g., by mixing solutions containing equimolar amounts of the free base and desired acid, and the required salt is collected by filtration, if insoluble, or by evaporation of the solvent.

The compounds of the formula (I) and their pharmaceutically acceptable salts are antifungal agents, useful in combating fungal infections in animals, including humans. For example, they are useful in treating topical fungal infections in man caused by, among other organisms, species of *Candida, Trichophyton, Microsporum* or *Epidermophyton,* or in mucosal infections caused by *Candida albicans* (e.g., thrush and vaginal candidiasis). They can also be used in the treatment of systemic fungal infections caused by, for example, *Candida Cryptococcus neoformans, Aspergillus fumigatus, Coccidioides, Paracoccidioides, Histoplasma* or *Blastomyces.*

The in vitro evaluation of the antifungal activity of the compounds can be performed by determining the minimum inhibitory concentration (m.i.c.) of the test compounds in a suitable medium at which growth of the particular microorganism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other microorganisms used in such tests can include *Cryptococcus neoformans, Aspergillus fumigatus, Trichophyton* spp; *Microsporum* spp; *Epidermophyton floccosum, Coccidioides immitis* and *Torulopsis glabrata.*

The in vivo evaluation of the compounds can be carried out at a series of dose levels by intraperitoneal or intravenous injection or by oral administration, to mice which are inoculated with a strain of *Candida albicans.* Activity is based on the survival of a treated group of mice after the death of an untreated group of mice following 48 hours observation. The dose level at which the compound provides 50% protection against the lethal effect of the infection is noted.

For human use, the antifungal compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavoring or coloring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) will be from 0.1 to 10 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances wherein higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated at a concentration between 1 and 10%, into an ointment consisting of a white wax or white soft paraffin base together with such stabilizers and preservatives as may be required.

The compounds of the formula (I) and their salts also have activity against a variety of plant pathogenic fungi, including for example, various rusts, mildews and molds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Microorganisms used in such tests include *Cochliobolus carbonum, Pyricularia oryzae, Glomerella cingulata, Penicillium digitatum, Botrytis cinerea* and *Rhizoctonia solani*.

For agricultural and horticultural purposes the compounds and their agriculturally acceptable salts are preferably used in the form of a composition formulated as appropriate to the particular use and purpose desired. Thus the compounds may be applied in the form of dusting powders or granules, seed dressings, aqueous solutions, dispersions or emulsions, dips, sprays, aerosols or smokes. Compositions may also be supplied in the form of dispersible powders, granules or grains or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example, they can be applied directly to the plant foliage, stems, branches, seeds or roots or to the soil or other growing medium, and they may be used not only to eradicate disease, but also prophylactically to protect the plants or seeds from attack.

EXAMPLE 1

1,1-Bis(5-chloropyrid-2-yl)-2-(1H-1,2,4-triazol-1-yl)ethyl chloride hydrochloride To 2.0 g (5.95 mmoles) of 1,1-bis(5-chloropyrid-2-yl)-2-(1H-1,2,4-triazol-1-yl)ethanol and 2.4 g (35.3 mmoles) of imidazole in 60 ml. of acetonitrile was added with stirring 2.1 g (17.65 mmoles) of thionyl chloride, the reaction mixture stirred for 2 hrs at room temperature and the solvent allowed to evaporate. Dilute sodium bicarbonate solution (30 ml) was added to the residue and the mixture extracted with ethyl acetate (3×50 ml). The combined extracts were dried over magnesium sulfate, concentrated to dryness and the residue chromatographed on 230–400 mesh silica gel using ethyl acetate-petrol (b.p. 60°–80° C.) (1:1, v:v) as the eluent. The fractions containing the product were combined and concentrated in vacuo to a colorless oil. Treatment of the residue with ethereal hydrogen chloride gave 1.4 (60% yield) of the desired product as a white solid, m.p. 115°–125° C.

Anal. Calcd. for $C_{14}H_{10}Cl_3N_5 \cdot HCl$: C, 43.0; H, 2.8; N, 17.9. Found: C, 43.0; H, 3.0; N, 17.7.

EXAMPLE 2

1-(5-Chloropyrid-2-yl)-1-(2,4-dichlorophenyl)-2-(1H-1,2,4-triazol-1-yl)ethyl chloride hydrochloride 1-(5-Chloropyrid-2-yl)-1-(2,4-dichlorophenyl)-2-(1H-1,2,4-triazol-1-yl)ethanol (750 mg, 2.03 mmoles) and imidazole (840 mg, 12.35 mmoles) were stirred in 30 ml of acetonitrile while 720 mg of thionyl chloride was added. The reaction mixture was stirred for 18 hrs. at room temperature and the solvent was then evaporated. Dilute sodium bicarbonate solution (10 ml) was added to the residue and the mixture extracted with ethyl acetate (4×20 ml). The combined extracts were dried over magnesium sulfate, evaporated under vacuum and the residue chromatographed on 230–400 mesh silica gel using ethyl acetate-petrol (b.p. 60°–80° C.) (1:1, v:v). The fractions containing the product were combined and concentrated to dryness to give the product as a colorless gum. Treatment of the residue with ethereal hydrogen chloride gave the hydrochloride salt which was recrystallized from methanol-diisopropyl ether, 240 mg (28% yield), m.p. 120°–140° C.

Anal. Calcd. for $C_{15}H_{10}Cl_4N_4 \cdot HCl$: C, 42.4; H, 2.6; N, 13.2. Found: C, 42.8; H, 2.7; N, 13.5.

EXAMPLE 3

1-(5-Chloropyrid-2-yl)-1-(2,4-dichlorophenyl)-2-(1H-1,2,4-triazol-1-yl)ethyl bromide hydrochloride 1-(5-Chloropyrid-2-yl)-1-(2,4-dichlorophenyl)-2-(1H-1,2,4-triazol-1-yl)ethanol (0.55 g, 1.49 mmoles) was stirred in acetonitrile (20 ml) and thionyl bromide (0.4 g, 1.92 mmoles) was added. After 1 hr. at room temperature, a small amount of starting material remained (as shown by t.l.c.) and thus a further 0.1 g of thionyl bromide was added and the solution was stirred overnight at room temperature. The acetonitrile was then removed by evaporation under reduced pressure and the residue was basified with aqueous sodium bicarbonate solution and extracted with ethyl acetate (3×40 ml). The combined organic extracts were dried over magnesium sulfate and evaporated and the residue was flash chromatographed on silica (230–400 mesh), eluting with ethyl acetate:hexane (1:3, v:v) to give an oil which was dissolved in dry ether and treated with ethereal hydrogen chloride. The white solid which precipitated (0.23 g) was recrystallized from isopropanol/diisopropyl ether to give the title compound as white crystals, 0.112 g (16%), m.p. 130°–150° C.

Anal. Calcd. for $C_{15}H_{10}BrCl_3N_4 \cdot HCl$: C, 38.4; H, 2.4; N, 12.0. Found: C, 38.6; H, 2.5; N, 11.9.

EXAMPLE 4

1,1-Bis(5-chloropyrid-2-yl)-2-(1H-1,2,4-triazol-1-yl)ethyl bromide hydrochloride Following the procedure of Example 3, and starting with the appropriate reagents, the titled compound was prepared in 33% yield, m.p. 111°–115° C.

Anal. Calcd. for $C_{14}H_{10}BrCl_2N_5 \cdot HCl$: C, 38.6; H, 2.6; N, 16.1. Found: C, 38.8; H, 2.6; N, 16.1.

EXAMPLE 5

The following illustrate pharmaceutical compositions for the treatment of fungal infections:

(a) Capsule: 71 parts by weight of the compound of Example 1 are granulated with 3 parts maize starch and 22 parts lactose and then a further 3 parts maize starch and 1 part magnesium stearate are added. The mixture is regranulated and filled into hard gelatin capsules.

(b) Cream: 2 parts by weight of the compound of Example 1 are dissolved in 10 parts of propylene glycol and mixed into 88 parts of a vanishing cream base.

(c) Pessary: 2 parts by weight of the compound of Example 2 are suspended in 98 parts of a warm liquified suppository base which is poured into molds and allowed to solidify.

The following Preparations illustrate the preparation of certain starting materials. All temperatures are in °C.

PREPARATION 1

(a) Preparation of bis-(5-chloropyrid-2-yl)ketone

A solution of n-butyllithium in hexane (16.3 ml, 1.55 molar) was added under nitrogen to a stirred solution of 2-bromo-5-chloropyridine (5 g) in dry diethyl ether (70 ml) at −70° C. over a period of 20 minutes. A solution of dimethylcarbamoylchloride (1.36 g) in dry diethyl ether (25 ml) was then added slowly over a period of 20 minutes. The mixture was stirred for a further 20 minutes at −70° C. and a solution of ammonium chloride (5 g) in water (50 ml) was then added and the solution allowed to warm to room temperature. The ether layer was separated and the aqueous solution extracted with diethyl ether (2×50 ml). The ether extracts were combined, dried over magnesium sulfate and evaporated. The residue was chromatographed on silica, eluting with a mixture of ethyl acetate and petroleum ether b.p. 60°–80° C. (1:9). The relevant fractions were combined and evaporated and the residue triturated with diethyl ether and dried to yield the title compound as a buff colored solid (0.86 g), (27%), m.p. 164°–167° C.

Anal. Calcd. for $C_{11}H_6Cl_2N_2O$: C, 52.2; H, 2.3; N, 11.1 Found: C, 52.4; H, 2.5; N, 11.0

(b) Preparation of 2,2-bis-(5-chloro-pyrid-2-yl)oxirane

A mixture of bis-(5-chloropyrid-2-yl)ketone (0.8 g), trimethylsulphoxonium iodide (0.84 g), cetrimide (0.08 g) and sodium hydroxide (3 g) in water (16 ml) and 1,1,1-trichloroethane (30 ml) was stirred vigorously and heated at 70° to 75° C. for 2.5 hours. Further trimethylsulphoxonium iodide (0.86 g) was added and the mixture heated at 75° to 80° C. for a further 2 hours. The mixture was cooled, diluted with water (10 ml) and extracted with dichloromethane (3×20 ml). The combined organic extracts were dried over magnesium sulfate and evaporated to yield the crude title compound as a brownish paste (0.8 g), which was used directly.

(c) 1,1-Bis-(5-chloropyrid-2-yl)-2-(1H-1,2,4-triazol-1-yl)ethanol 2,2-Bis(5-chloro-pyrid-2-yl)oxirane (0.8 g), 1,2,4-triazole (1.0 g) and anhydrous potassium carbonate (3.0 g) were stirred in dry N,N-dimethylformamide (30 ml) and the mixture was heated at 85° C. for 1.5 hours. The solvent was then evaporated under vacuum, with the addition of xylene to remove final traces of N,N-dimethylformamide as an azeotrope, and the residue was dissolved in water (20 ml) and extracted with ethyl acetate (3×20 ml). The combined organic extracts were dried over megnesium sulfate and evaporated. The residue was chromatographed on silica, eluting with ethyl acetate. Evaporation of the relevant fractions gave a viscous oil which solidified on trituration with petroleum ether (b.p. 60°–80° C.). Recrystallization from hexane gave the title compound as white crystals (0.48 g, 38%) m.p. 98°–100° C.

Anal. Calcd. for $C_{14}H_{11}Cl_2N_5O$: C, 50.0; H, 3.3; N, 20.8. Found: C, 50.2; H, 3.3; N, 20.6.

PREPARATION 2

Preparation of 1-(5-Chloropyrid-2-yl)-1-(2,4-dichlorophenyl)-2-(1H-1,2,4-triazol-1-yl)ethanol A solution of 2-bromo-5-chloropyridine (3 g, 15.6 mmoles) in diethylether (70 ml) was stirred and cooled to −68° C. A solution of n-butyllithium in hexane (1.55 m, 9.6 ml, 14.9 mmoles) was added dropwise over 20 minutes and the reaction mixture was stirred for a further 15 minutes at −68° C. after the addition was complete. A solution of 2,2',4'-trichloroacetophenone (2.8 g, 12.53 mmoles) in diethylether (40 ml) was then added dropwise over 30 minutes and stirring was continued at −68° C. for a further 1.5 hours. Glacial acetic acid (3 ml) was then added followed by water (20 ml) and the mixture was stirred for 5 minutes. The diethylether layer was then decanted off, water was added to the residue and the mixture was allowed to warm until the ice had melted. Extraction of this aqueous layer with diethylether, followed by drying (magnesium sulphate) and evaporation of the combined diethylether extracts gave an orange oil (7 g) which was treated directly with a mixture of 1,2,4-triazol (5 g, 72.5 mmoles) and anhydrous potassium carbonate (20 g, 0.145 mole) in dimethylformamide (70 ml) and the mixture was stirred at 85° C. for 18 hours. The solvent was then evaporated, water was added to the residue and the mixture was extracted with ethyl acetate. The combined organic extracts were dried (magnesium sulphate) and evaporated to give a red oil (6 g) which was chromatographed on silica (230–400 mesh), eluting with hexane:isopropanol, 90:10, to give after one recrystallization from cyclohexane., the title compound, 0.32 g (7%), m.p. 149°–150° C.

Anal. Calcd. for $C_{15}H_{11}Cl_3N_4O$: C, 48.7; H, 3.0; N, 15.2. Found: C, 48.5; H, 3.0; N, 15.1.

We claim:

1. A compound having the formula

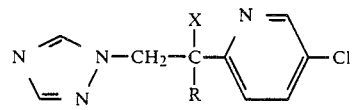

or a pharmaceutically acceptable acid addition salt thereof where X is selected from the group consisting of chloro and bromo and R is 5-chloropyrid-2-yl.

2. The compound of claim 1, wherein X is chloro.

3. The compound of claim 1, wherein X is bromo.

* * * * *